(12) United States Patent
Kohara

(10) Patent No.: US 10,302,487 B2
(45) Date of Patent: May 28, 2019

(54) NOISE REDUCTION APPARATUS AND DETECTION APPARATUS INCLUDING THE SAME

(71) Applicant: CANON KABUSHIKI KAISHA, Tokyo (JP)

(72) Inventor: Naoki Kohara, Kawasaki (JP)

(73) Assignee: CANON KABUSHIKI KAISHA, Tokyo (JP)

(*) Notice: Subject to any disclaimer, the term of this patent is extended or adjusted under 35 U.S.C. 154(b) by 0 days.

(21) Appl. No.: 16/151,013

(22) Filed: Oct. 3, 2018

(65) Prior Publication Data

US 2019/0033131 A1    Jan. 31, 2019

Related U.S. Application Data

(63) Continuation of application No. 15/823,421, filed on Nov. 27, 2017, now Pat. No. 10,132,681.

(30) Foreign Application Priority Data

Nov. 29, 2016 (JP) .................... 2016-231770
Oct. 27, 2017 (JP) .................... 2017-208430

(51) Int. Cl.
*G01J 3/44* (2006.01)
*G01J 3/02* (2006.01)
*G01N 21/65* (2006.01)
*H01S 3/00* (2006.01)
*H01S 3/108* (2006.01)
*H01S 3/23* (2006.01)
*G01J 3/433* (2006.01)

(52) U.S. Cl.
CPC .......... *G01J 3/0297* (2013.01); *G01J 3/0208* (2013.01); *G01J 3/0218* (2013.01); *G01J 3/0224* (2013.01); *G01J 3/0262* (2013.01); *G01J 3/433* (2013.01); *G01J 3/44* (2013.01); *G01N 21/65* (2013.01); *H01S 3/0078* (2013.01); *H01S 3/1086* (2013.01); *H01S 3/2391* (2013.01); *G01N 2021/655* (2013.01); *G01N 2021/656* (2013.01)

(58) Field of Classification Search
CPC .... G01J 3/02; G01J 3/44; G01J 3/433; G01N 21/65; G01N 21/64; H01S 3/108; H01S 3/00; H01S 3/23
See application file for complete search history.

(56) References Cited

U.S. PATENT DOCUMENTS

2017/0219489 A1* 8/2017 Cheshnovsky ........ G02B 21/00

FOREIGN PATENT DOCUMENTS

JP        5623652 B2     11/2014
WO     2016/079845 A1    5/2016

* cited by examiner

*Primary Examiner* — Abdullahi Nur
(74) *Attorney, Agent, or Firm* — Canon U.S.A., Inc. IP Division

(57) ABSTRACT

A noise reduction apparatus includes a first delaying/combining unit configured to output first and second pulse light beams, and a second delaying/combining unit configured to branch the first pulse light beam into two pulse light beams to output third and fourth pulse light beams and branch the second pulse light beam into two pulse light beams to output fifth and sixth pulse light beams.

26 Claims, 11 Drawing Sheets

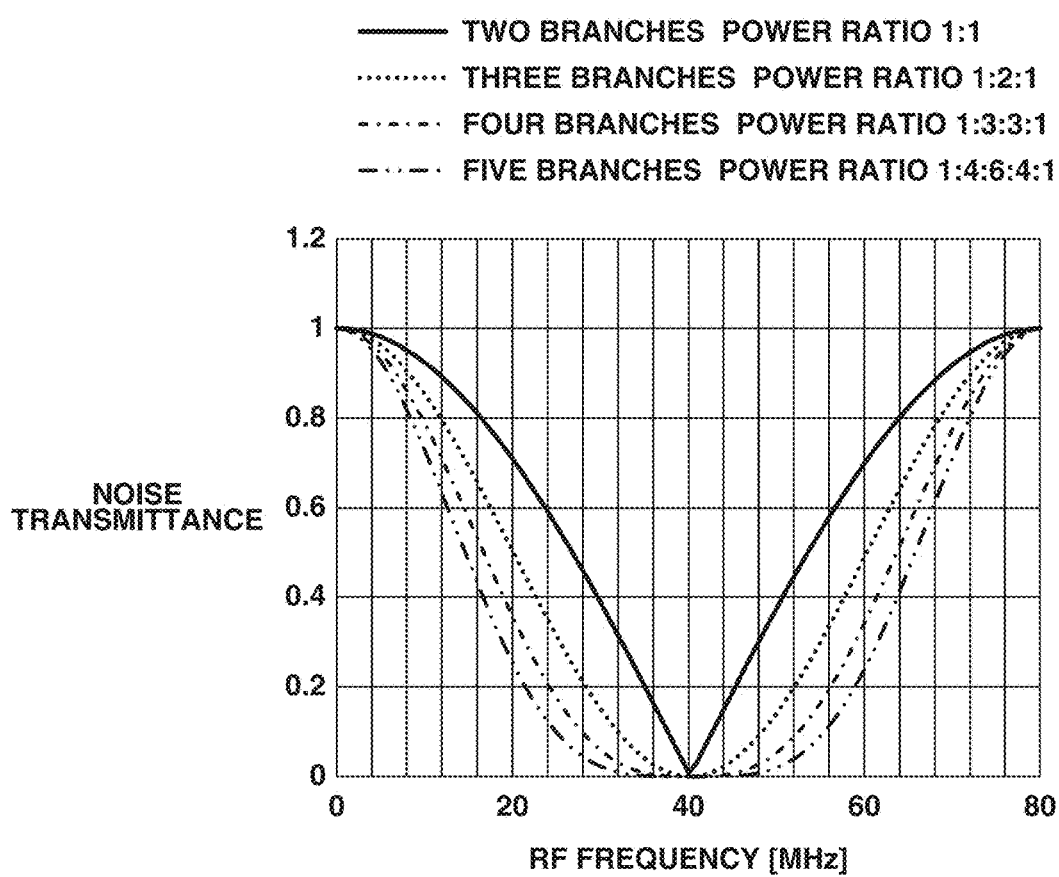

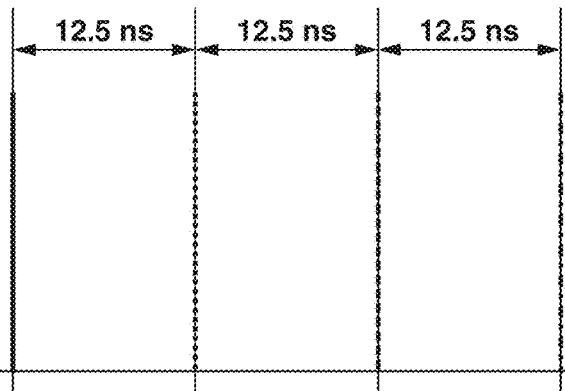
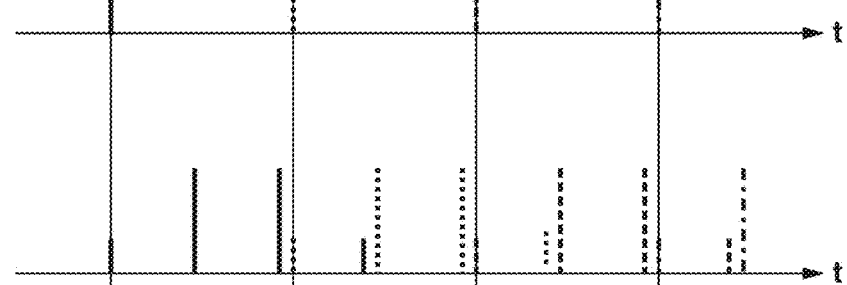
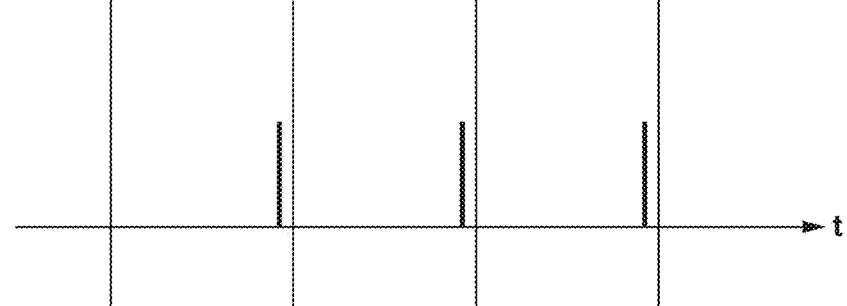
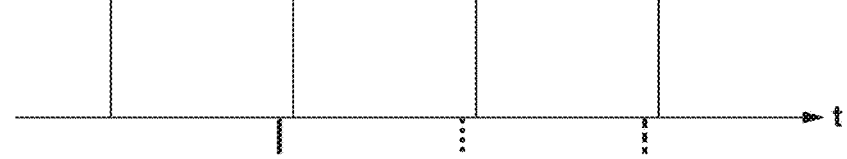
FIG.9A
FIG.9B
FIG.9C
FIG.9D

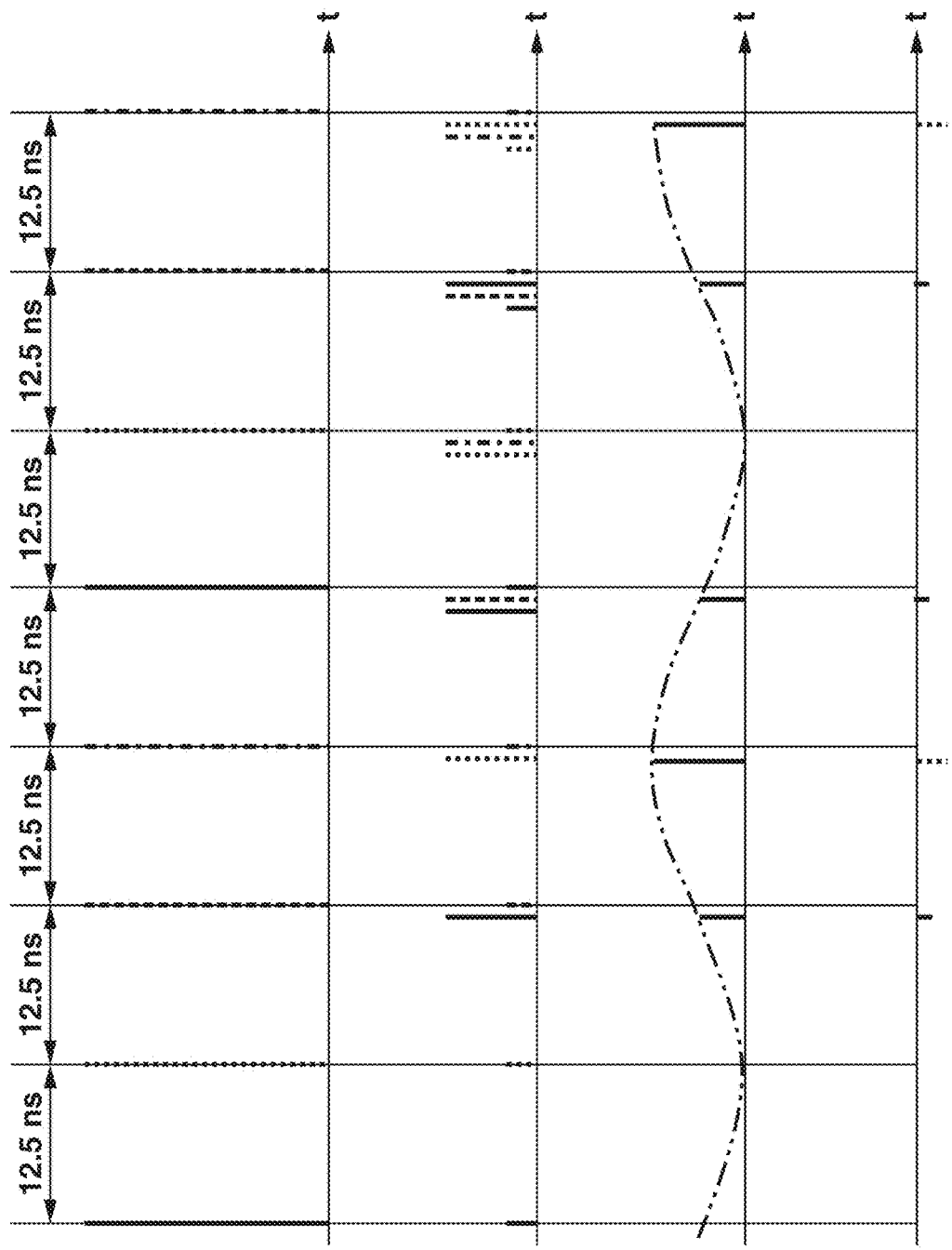

NOISE REDUCTION APPARATUS AND DETECTION APPARATUS INCLUDING THE SAME

CROSS-REFERENCE TO RELATED APPLICATION

This application is a Continuation of U.S. application Ser. No. 15/823,421, filed Nov. 27, 2017, which claims priority from Japanese Patent Application No. 2016-231770, filed Nov. 29, 2016, and Japanese Patent Application No. 2017-208430, filed Oct. 27, 2017, which are hereby incorporated by reference herein in their entireties.

BACKGROUND OF THE INVENTION

Field of the Invention

The aspect of the embodiments relates to noise reduction apparatuses and, in particular, relates to noise reduction apparatuses for use in detection apparatuses such as stimulated Raman scattering (SRS) microscopes.

Description of the Related Art

In recent years, Raman scattering detection apparatuses using a non-linear optical process have been discussed as an apparatus which realizes a shorter detection time than spontaneous Raman scattering detection apparatuses. Japanese Patent No. 5623652 discusses a stimulated Raman scattering (SRS) microscope as a non-linear Raman scattering detection apparatus. This SRS microscope irradiates a sample with two-color pulse light beams of different light frequencies (wavelengths) and lock-in detects a generated intensity modulation of the pulse light beam as a SRS signal to identify and distinguish molecules contained in the sample.

Further, the SRS microscope discussed in Japanese Patent No. 5623652 reduces intensity noise in pulse light beams by dividing one optical path of the two-color pulse light beams into two optical paths, delaying one of the divided pulse light beams, and then combining the pulse light beams.

WO/2016/079845 discusses a noise reduction apparatus capable of reducing noise over a wider frequency range around a specific frequency corresponding to a delay time by providing a specific delay and intensity ratio to pulse light beams divided into not two but a plurality of pulse light beams.

In a case of measuring SRS signals at a high speed, the frequency band of signals acquired through lock-in detection is broader. However, the technique discussed in Japanese Patent No. 5623652 can reduce noise only with respect to a limited frequency band, so that it is difficult to sufficiently reduce noise over a broad band. The technique discussed in WO/2016/079845 attempts to address the situation by combining a plurality of delayed pulse light beams. However, when the plurality of divided pulse light beams is coaxially combined (or guided to a single-mode fiber) for use in microscopes, in general there arises a situation of light amount loss. Light amount loss leads to a decrease in signals, which reduces the signal-to-noise (S/N) ratio of detected signals (the technique discussed in WO/2016/079845 increases the S/N ratio by reducing more noise compared with a decrease in signals). For example, stimulated Raman scattering (and signals thereof) occurs proportional to the product of intensities of pulse light beams incident on a sample.

SUMMARY OF THE INVENTION

According to an aspect of the embodiments, a noise reduction apparatus configured to reduce noise in a pulse light beam of a first period includes a first delaying/combining unit configured to branch the pulse light beam of the first period into two pulse light beams, provide a first delay time between the two branched pulse light beams, and combines the two branched pulse light beams, to output a first pulse light beam polarized in a first direction and a second pulse light beam polarized in a direction orthogonal to the first direction and delayed by the first delay time with respect to the first pulse light beam, and a second delaying/combining unit configured to branch the first pulse light beam into two pulse light beams, provide a second delay time between the two branched pulse light beams, combines the two branched pulse light beams, to output a third pulse light beam polarized in a second direction and a fourth pulse light beam polarized in a direction orthogonal to the second direction and delayed by the second delay time with respect to the third pulse light beam, branch the second pulse light beam into two pulse light beams, provide the second delay time between the two branched pulse light beams, and combines the two branched pulse light beams, to output a fifth pulse light beam polarized in the second direction and a sixth pulse light beam polarized in a direction orthogonal to the second direction and delayed by the second delay time with respect to the fifth pulse light beam, wherein the light intensity ratio between the first pulse light beam and the second pulse light beam is 1:1, the light intensity ratio between the third pulse light beam and the fourth pulse light beam is 1:3, the light intensity ratio between the fifth pulse light beam and the sixth pulse light beam is 3:1, and the ratio between the first delay time and the second delay time is 1:2 or 2:1.

Further features of the disclosure will become apparent from the following description of exemplary embodiments with reference to the attached drawings.

BRIEF DESCRIPTION OF THE DRAWINGS

FIG. 4 illustrates a noise reduction rate.

FIGS. 9A to 9D illustrate time profiles of optical pulse trains of the SRS microscope according to Example 2.

FIGS. 11A to 11D illustrate time profiles of optical pulse trains of the SRS microscope according to Example 3.

DESCRIPTION OF THE EMBODIMENTS

Figure 1:
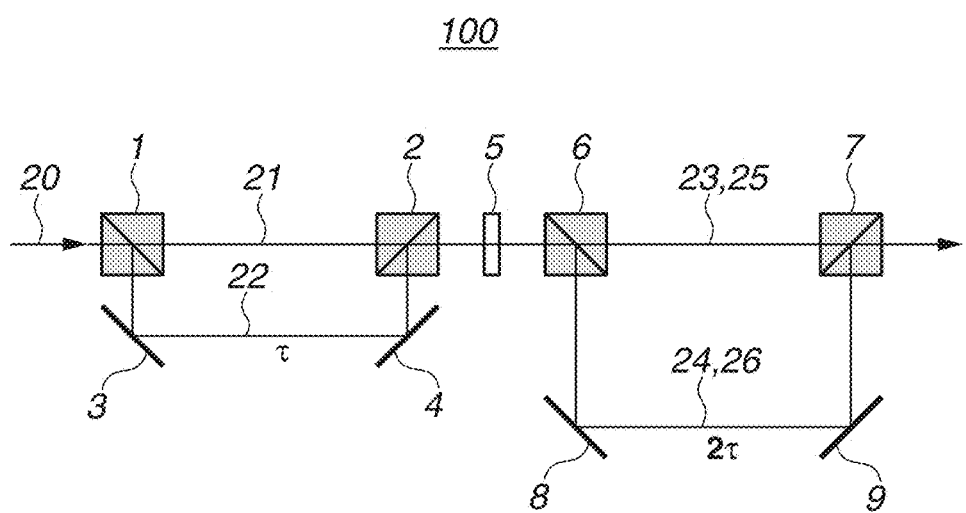
FIG. 1 schematically illustrates an example of the structure of a noise reduction apparatus (first exemplary embodiment).

A noise reduction apparatus 100 according to a first exemplary embodiment will be described below with reference to the attached drawings. FIG. 1 schematically illustrates the structure of the noise reduction apparatus 100. The noise reduction apparatus 100 reduces noise around a specific frequency contained in pulse light beams emitted from a light source such as a pulse laser through two delaying/combining optical paths using polarization beam splitters. According to the present exemplary embodiment, pulse trains at the light intensity ratio of 1:3:3:1 are generated from incident pulse light beams at regular time intervals with reduced light amount loss (with no loss except for the loss associated with the reflectance and transmittance of optical devices).

An incident pulse light beam 20 is divided (branched) by a polarization beam splitter 1 into a pulse light beam 21 (first pulse light beam) and a pulse light beam 22 (second pulse light beam). The pulse light beams 21 and 22 have the same light intensity (pulse energy). In a case where the incident pulse light beam 20 is polarized, a polarization adjustment unit (not illustrated) rotates the polarization direction to adjust the polarization direction to 45 degrees so that a polarization beam splitter divides an incident light beam into linearly-polarized light beams (P-polarized light, S-polarized light) in two directions which are orthogonal to each other. For example, the polarization direction is adjusted using a half-wave plate such that the amplitudes (or light intensity) of an electric field in a direction of the sheet of FIG. 1 and in a perpendicular direction with respect to the direction of the sheet become equal. Further, a light source (e.g., pulse laser) which generates the incident pulse light beam 20 can be adjusted, or the delaying/combining optical paths including the polarization beam splitters can be rotated about the optical axis.

The pulse light beams 21 and 22 travel through different optical paths and are combined coaxially by a polarization beam splitter 2. The optical path lengths between the polarization beam splitters 1 and 2 are adjusted using mirrors 3 and 4 such that the optical path length of the pulse light beam 22 is greater by $\Delta L$ than the optical path length of the pulse light beam 21. Thus, after the combining the pulse light beam 22 is delayed by $\tau$ ($=\Delta L/c$, where c is the speed of light) with respect to the pulse light beam 21.

Figure 2:
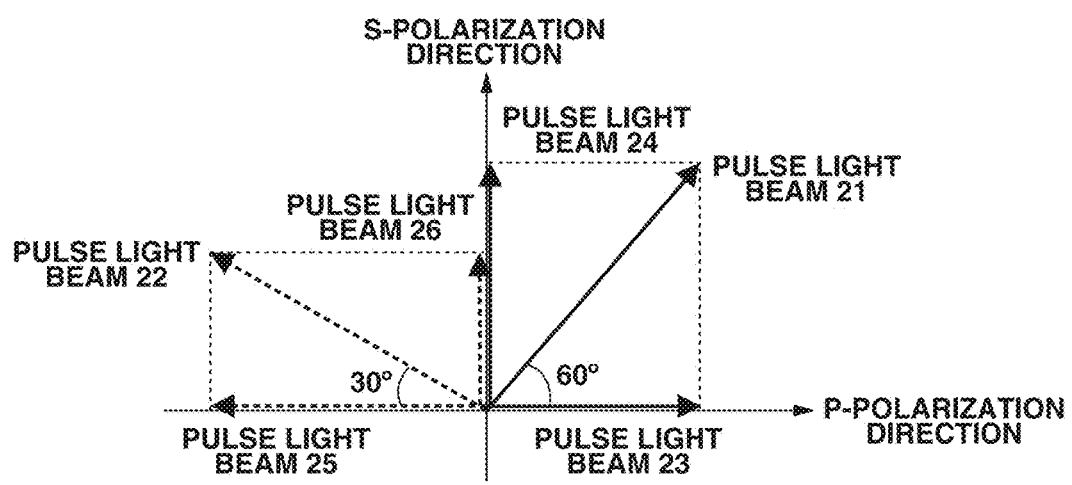
FIG. 2 illustrates polarization directions of pulse light beams.

The combined pulse light beam is passed through a polarization adjustment unit 5 to rotate the polarization direction by 60 degrees. The polarization direction of the pulse light beam is rotated by 60 degrees to adjust the intensity ratio of the light beams to be divided by a polarization beam splitter 6 to 1:3 (1:$\sqrt{3}$ in terms of the ratio of absolute values of the electric field) as illustrated in FIG. 2. In FIG. 2, the vertical axis is the direction which is parallel to a polarization separation plane of the polarization beam splitters and orthogonal to the optical axis (S-polarization direction), and the horizontal axis is the direction which is orthogonal to the S-polarization direction and the optical axis (P-polarization direction). The pulse light beam 21 which passes through the polarization beam splitter 2 as P-polarized light is divided into a pulse light beam 23 (third pulse light beam) and a pulse light beam 24 (fourth pulse light beam) at a light intensity ratio of 1:3.

The pulse light beams 23 and 24 travel through different optical paths and are coaxially combined by a polarization beam splitter 7. The optical path lengths between the polarization beam splitters 6 and 7 are adjusted using mirrors 8 and 9 such that the optical path length of the pulse light beam 24 is greater by $2\Delta L$ than the optical path length of the pulse light beam 23. Thus, after the combining the pulse light beam 24 is delayed by $2\tau$ ($=2\Delta L/c$, where c is the speed of light) with respect to the pulse light beam 23. Specifically, the arrangement is made such that the ratio of a delay time (first delay time) provided by a first delaying/combining optical path including the polarization beam splitters 1 and 2 to a delay time (second delay time) provided by a second delaying/combining optical path including the polarization beam splitters 6 and 7 is adjusted to 1:2.

Next, the pulse light beam 22 which arrives at a time delayed by $\tau$ with respect to the pulse light beam 21 will be discussed below. The polarization direction of the pulse light beam 22 is rotated by 60 degrees by the polarization adjustment unit 5 as in the case of the pulse light beam 21. As illustrated in FIG. 2, even after the polarization direction is rotated, the pulse light beam 22 is orthogonal to the pulse light beam 21. Thus, the pulse light beam 22 reflected as S-polarized light from the polarization beam splitter 2 is divided by the polarization beam splitter 6 into a pulse light beam 25 (fifth pulse light beam) and a pulse light beam 26 (sixth pulse light beam) at the light intensity ratio of 3:1.

The pulse light beams 25 and 26 travel through different optical paths and are coaxially combined by the polarization beam splitter 7. The pulse light beam 25 travels through the same optical path as the optical path of the pulse light beam 23, whereas the pulse light beam 26 travels through the same optical path as the optical path of the pulse light beam 24. When the pulse light beam 21 is divided, the pulse light beam 23 showing a small light intensity travels through the short optical path. On the other hand, when the pulse light beam 22 is divided, the pulse light beam 26 showing a small light intensity travels through the long optical path. Further, since the delay time ratio between the first and second delaying/combining optical paths is set to 1:2, pulse light beams at the light intensity ratio of 1:3:3:1 are emitted from the polarization beam splitter 7 at regular time intervals.

Figure 3A:
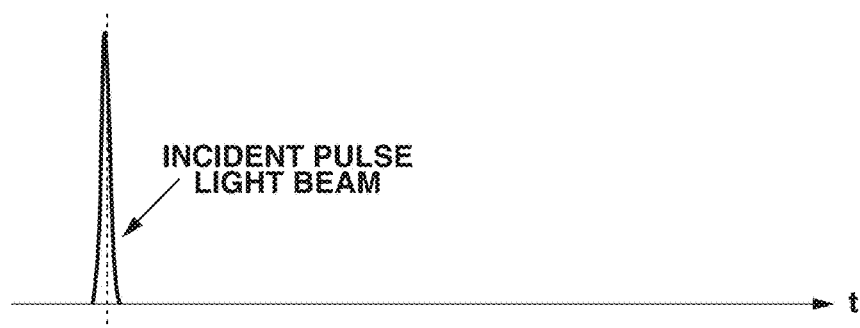
FIGS. 3A to 3C illustrate time profiles of pulse light beams.
Figure 3B:
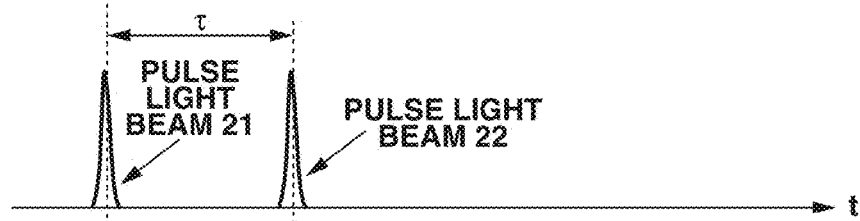
Figure 3C:
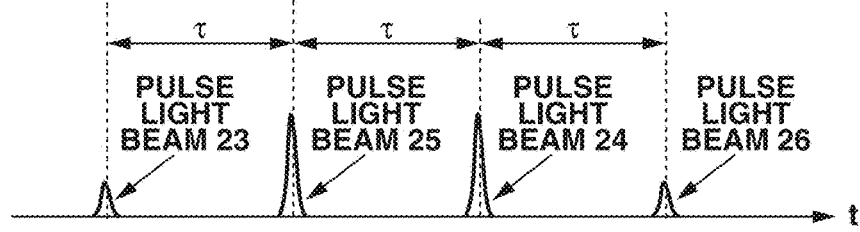

This will be described below with reference to FIGS. 3A to 3C which illustrate time profiles of the pulse light beams. FIG. 3A illustrates the time profile of the incident pulse light beam. FIG. 3B illustrates the time profiles of the pulse light beams 21 and 22. FIG. 3C illustrates the time profiles of the pulse light beams 23, 24, 25, and 26. The incident pulse light beam illustrated in FIG. 3A is divided by the first delaying/combining optical path into pulse light beams at a time interval $\tau$ as illustrated in FIG. 3B. Further, the pulse light beam is divided by the second delaying/combining optical path into pulse light beams at the light intensity ratio of 1:3:3:1 at the time interval $\tau$.

The pulse light beam in FIG. 3A is repeatedly incident at a frequency determined by the length of a resonator such as a pulse laser, so that each incident pulse is divided into four pulses as illustrated in FIG. 3C.

The noise reduction at the light intensity ratio of 1:3:3:1 will be described below. Noise contained in a pulse light beam output from the noise reduction apparatus is represented by formula (1) as a function of frequency f (noise power of an incident light beam per unit frequency at the frequency f is 1, and pulse light beams do not overlap in time, i.e., pulse light beams do not interfere with each other).

$$|1/8 + 3e^{(i2\pi f\tau)}/8 + 3e^{(i4\pi f\tau)}/8 + e^{(i6\pi f\tau)}/8| = \{(1+\cos 2\pi f\tau)/2\}^{3/2} \qquad \text{formula (1)}$$

A phase component corresponding to the frequency f and the delay time $\tau$ is introduced to each of four pulse light beams with intensities of 1/8, 3/8, 3/8, and 1/8, and the absolute value of the summation of each item is calculated to express the noise reduction rate of the noise reduction apparatus. At frequency $f=(2m-1)/(2\tau)$, where m is an integer, noise is completely cancelled. At frequencies near $f=(2m-1)/(2\tau)$, noise is reduced according to formula (1). To realize reduction of noise over a wide range of frequencies near frequency fr, the noise reduction apparatus is set such that $\tau=1/(2 \cdot fr)$, where m=1.

FIG. 4 is a citation of FIG. 3 of WO/2016/079845 which illustrates a comparison of noise transmittance spectra of the cases of two, three, four, and five branches with the power ratio taken into consideration. The plot of the four branches in FIG. 4 shows the result of formula (1) when $\tau=12.5$ nanoseconds. FIG. 4 indicates that 60% or more of noise is reduced in the 40 MHz frequency range around 40 MHz at which noise is completely canceled.

The light intensity ratio does not have to be exactly 1:3:3:1. In other words, the light intensity ratio may be approximately 1:3:3:1. For example, in a case in which the light intensity of one pulse light beam is increased to become 10% higher than the light intensity before the dividing and therefore the light intensity ratio changes to 1:3.8:3:1, noise in the increased portion is not canceled, so that the minimum value in the noise transmittance illustrated in FIG. 3C is not zero but 0.1. Accordingly, the noise reduction effect is still produced even if the light intensity ratio deviates from 1:3:3:1.

When three or more light beams having traveled through different optical paths are coaxially combined using a polarization beam splitter and a half mirror, in general light amount loss occurs (i.e., there occurs a light beam output in a direction other than the direction in which the light beam is intended to be output by the polarization beam splitter and the half mirror).

According to WO/2016/079845, two optical paths divided by polarization are further divided by polarization to generate a pulse light beam with an adjusted delay time and adjusted light intensity. In the case of division into three parts, an incident pulse light beam is first divided into pulse light beams A and B. The pulse light beam B is divided into pulse light beams C and D, and the pulse light beams C and D travel through different optical path lengths and are then combined by the polarization beam splitter. The polarization directions of the combined pulse light beams C and D are orthogonal to each other. The pulse light beams C and D are combined with the pulse light beam A, whereby noise reduction is realized. At this time, the pulse light beams C and D are output as one-directional polarized light beams by the polarization beam splitter. Specifically, two one-directional pulse light beams are generated from two two-directional pulse light beams which are orthogonal to each other. Consequently, only a half of the amount of incident light of the pulse light beams C and D is combined with the pulse light beam A and output. The light amount loss is undesirable when the output power of a light source such as a pulse laser is restricted or when the amount of light is intended to be increased as much as possible to improve the S/N ratio of signals.

According to the present exemplary embodiment, not only noise reduction over a wide frequency band is realized but also delaying/combining units for dividing a light beam into two beams are arranged in series to reduce light amount loss during the combining of the light beams (except for the loss associated with the transmittance and reflectance of the polarization beam splitters).

As the polarization adjustment unit 5 according to the present exemplary embodiment, for example, a half-wave plate can be used. The angle of the half-wave plate is set such that the angle of the polarization direction of the pulse light beam 21 with respect to the fast axis or slow axis is adjusted to 30 degrees. Further, the angle of the half-wave plate can be adjusted such that the ratio of the light intensity of the pulse light beam 23 evaluated by shielding the pulse light beams 22 and 24 to the light intensity of the pulse light beam 24 evaluated by shielding the pulse light beams 22 and 23 is adjusted to 1:3. Further, light beams output from the noise reduction apparatus 100 can be evaluated with a spectrum analyzer, etc. to adjust the angle of the half-wave plate to minimize noise. The polarization adjustment unit 5 is capable of rotating polarization directions and a Fresnel rhomb waveplate or the like can also be used other than the half-wave plate.

While an exemplary embodiment of the disclosure is described above, the disclosure is not limited to the disclosed exemplary embodiment, and various modifications and changes can be made within the spirit of the disclosure.

For example, the polarization beam splitters 1 and 6 can be replaced with a half mirror configured to divide a light beam in two directions at the light intensity ratio of 1:1. In this case, the divided light beams have the same polarization direction, so that in order to combine the light beams using the polarization beam splitter without light amount loss, a device (e.g., half-wave plate) for rotating the polarization direction by 90 degrees may be introduced to one of the divided optical paths.

Further, while the first delay time is $\tau$ and the second delay time is $2\tau$ in the above description, a similar noise reduction apparatus can be obtained even if the first delay time is set to $2\tau$ and the second delay time to $\tau$. Even in this case, pulse light beams at the light intensity ratio of 1:3:3:1 are generated at regular time intervals (only the order of polarization directions is changed), so that noise reduction performance remains the same.

Figure 5:
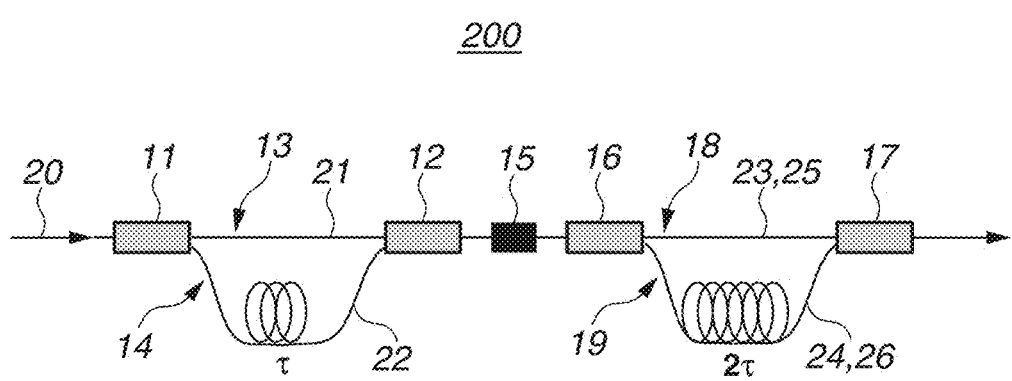
FIG. 5 schematically illustrates an example of the structure of a noise reduction apparatus (second exemplary embodiment).

A noise reduction apparatus 200 according to a second exemplary embodiment will be described below with reference to the attached drawings. FIG. 5 schematically illustrates the structure of the noise reduction apparatus 200. As in the first exemplary embodiment, pulse trains at the light intensity ratio of 1:3:3:1 are generated at regular time intervals using two delaying/combining optical paths with reduced light amount loss (with no loss except for the loss associated with the reflectance and transmittance of optical devices).

The delaying/combining optical paths are formed using fiber-type polarization beam splitters 11, 12, 16, and 17, and noise near a specific frequency contained in a pulse light beam emitted from a light source such as a pulse laser is reduced using the two delaying/combining optical paths.

The incident pulse light beam 20 is divided by the fiber-type polarization beam splitter 11 into the pulse light beam 21 (first pulse light beam) and the pulse light beam 22 (second pulse light beam) which have the same light intensity (pulse energy), and the pulse light beams 21 and 22 are respectively guided to polarization maintaining fibers 13 and 14. In order to divide a light beam into beams having the same light intensity, the polarization direction of the incident pulse light beam 20 is set such that light intensities on the fast and slow axes of the polarization maintaining fibers are equal. The polarization direction can be adjusted using a polarization controller, or a polarized light beam before being guided by a collimator to a polarization maintaining fiber can be adjusted using a half-wave plate, etc.

The pulse light beams 21 and 22 travel through different polarization maintaining fibers and are guided by the fiber-type polarization beam splitter 12 into a single polarization maintaining fiber. The polarization maintaining fiber 14 is set longer by ΔL than the polarization maintaining fiber 13. Thus, after the combining the pulse light beam 22 is delayed by τ (=n·ΔL/c, where c is the speed of light, and n is the group refractive index of the optical fiber) with respect to the pulse light beam 21.

The combined pulse light beam is passed through a polarization adjustment unit 15 to rotate the polarization direction by 60 degrees. The polarization direction of the pulse light beam by 60 degrees is rotated to adjust the light intensity ratio of the light beam to be divided by the polarization beam splitter 16 to the ratio 1:3 (1:√3 in terms of the absolute value ratio of the electric field).

The pulse light beam 23 (third pulse light beam) and the pulse light beam 24 (fourth pulse light beam) divided at the light intensity ratio of 1:3 travel through polarization maintaining fibers 18 and 19, respectively, and are guided to a single polarization maintaining fiber by the fiber-type polarization beam splitter 17, and are output.

The polarization maintaining fiber 19 is set longer by 2ΔL than the polarization maintaining fiber 18. Thus, after the combining the pulse light beam 24 is delayed by 2τ (=2nΔL/c, where c is the speed of light, and n is the group refractive index of the optical fiber) with respect to the pulse light beam 23. Specifically, the arrangement is made such that the ratio of the delay time (first delay time) given by the first delaying/combining optical path to the delay time (second delay time) given by the second delaying/combining optical path is adjusted to the ratio 1:2. The first delaying/combining optical path includes the fiber-type polarization beam splitters 11 and 12, and the second delaying/combining optical path includes the fiber-type polarization beam splitters 16 and 17.

Next, the pulse light beam 22 which arrives at a time delayed by τ following the pulse light beam 21 is also divided into the pulse light beam 25 (fifth pulse light beam) and the pulse light beam 26 (sixth pulse light beam) at the light intensity ratio of 3:1, as in the first exemplary embodiment. In the end, pulse light beams at the light intensity ratio of 1:3:3:1 are output from the fiber type polarization beam splitter 17 at regular time intervals.

The time profiles of the pulse light beams and noise reduction effect are similar to those described above in the first exemplary embodiment with reference to FIGS. 3 and 4.

As the polarization adjustment unit 5 according to the present exemplary embodiment, for example, a bulk or paddle polarization controller can be used. Further, when an output light beam fiber of the fiber-type polarization beam splitter 12 is fused with an input optical fiber of the fiber-type polarization beam splitter 16, their fast axes (or slow axes) may be shifted from each other by 60 degrees, and the fused portion can be used as the polarization adjustment unit 5. At the fused portion, the polarization direction of light transmitted through the fibers can be changed. The fiber fusion angle can be fine-adjusted such that the light intensity ratio of the pulse light beams 23 and 24 transmitted through the fibers while the fibers are brought close to each other before the fusing, is 1:3 (or the pulse light beams 25 and 26 are at the light intensity ratio of 3:1). Further, output light beams of the noise reduction apparatus 200 may be evaluated using a spectrum analyzer, etc., and the fusion angle can be fine-adjusted to minimize an amount of noise.

While an exemplary embodiment of the disclosure is described above, the disclosure is not limited to the disclosed exemplary embodiment, and various modifications and changes can be made within the spirit of the disclosure.

For example, the fiber-type polarization beam splitters 11 and 16 can be replaced with a branching coupler which divides an input light beam at the light intensity ratio of 1:1 and guides the divided light beams respectively to two polarization maintaining fibers. In this case, the divided light beams have the same polarization direction, so that in order to combine the light beams without losing a light amount, a device for rotating the polarization direction by 90 degrees is introduced into one of the divided fibers. For example, either a polarization controller is further introduced, or a fused portion which combines and fuses the fast and slow axes may be included in the fiber.

Further, while the first delay time is τ and the second delay time is 2τ in the above description, a similar noise reduction apparatus can be obtained even if the first delay time is set to 2τ and the second delay time to τ. Even in this case, pulse light beams at the light intensity ratio of 1:3:3:1 are generated at regular time intervals (only the order of polarization directions is changed), so noise reduction performance remains the same.

Figure 6:
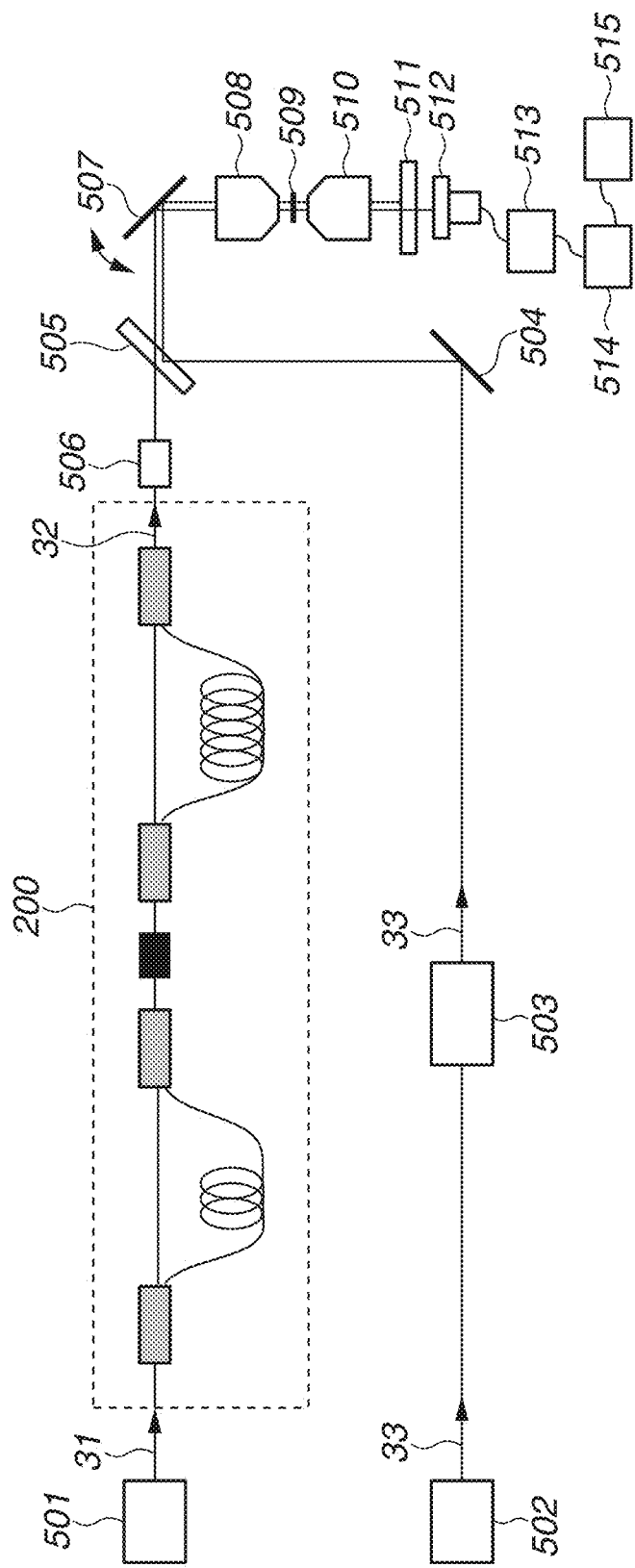
FIG. 6 is a conceptual diagram illustrating a stimulated Raman scattering (SRS) microscope according to Example 1.

A detection apparatus to which Example 1 of the disclosure is applied will be described below with reference to FIG. 6. A stimulated Raman scattering (SRS) microscope will be described as an example. The SRS microscope detects SRS generated in response to simultaneous irradiation of a sample with two light beams of different wavelengths. SRS is one of the non-linear optical phenomena and is generated proportional to the product of light intensities of wavelengths. Thus, in order to efficiently generate SRS, a single point on the sample is simultaneously irradiated with optical beams of lasers of two wavelengths. If SRS is generated, the intensity of the pulse light beam having the shorter wavelength decreases among the pulse light beams of two wavelengths while the intensity of the other pulse light beam having the longer wavelength increases. Further, in order to efficiently generate SRS and provide sufficient Raman spectral resolution, a short pulse laser having a pulse time width of 1 to 10 picoseconds is used. To detect SRS with great sensitivity, the periods of two pulse light beams are synchronized in the ratio 1:2 to produce a state in which a SRS signal is contained in each pulse of one of the pulse light beams. The SRS signals can be acquired with a lock-in amplifier using as a lock-in frequency a frequency (repeated laser frequency) corresponding to one of the two pulse light beams that has the longer pulse period. The noise reduction apparatus according to the present example reduces noise over a wide frequency region near the lock-in frequency to acquire the SRS signals with great sensitivity.

Optical pulse trains at the pulse period ratio of 1:2 are used as a pulse laser 501 (first generation unit) and a pulse laser 502 (second generation unit). A solid-state laser (titanium sapphire laser) having a center wavelength of 800 nanometers and a pulse period (first period) of 12.5 nanoseconds is used as the pulse laser 501. For example, a Spectra-Physics Mai Tai is used. An ytterbium-doped fiber laser having a center wavelength of 1030 nanometers and a pulse period of 25 nanoseconds is used as the pulse laser 502.

A SRS signal occurs with 25-nanosecond periods, so that in order to reduce noise over the widest frequency range near the lock-in frequency of 40 MHz, the time interval of pulse light beams divided by the noise reduction apparatus is set to 12.5 nanoseconds. To produce the time interval, a difference in fiber length in the first delaying/combining unit of the noise reduction apparatus 200 is set to 2.5 meters (the speed of light is $3 \times 10^8$ meters per second, and the group refractive index of optical fibers is 1.5). Further, a difference in fiber length in the second delaying/combining unit is set to 5 meters.

To cancel noise at the lock-in frequency, the time interval of pulse light beams may be set to (12.5+25·m) nanoseconds (m is an integer of zero or larger). However, the larger the value of m is, the narrower the frequency range over which noise can be reduced becomes, and the lengths of the optical fibers of the noise reduction apparatus are to be increased, so there is no merit.

Figure 7:
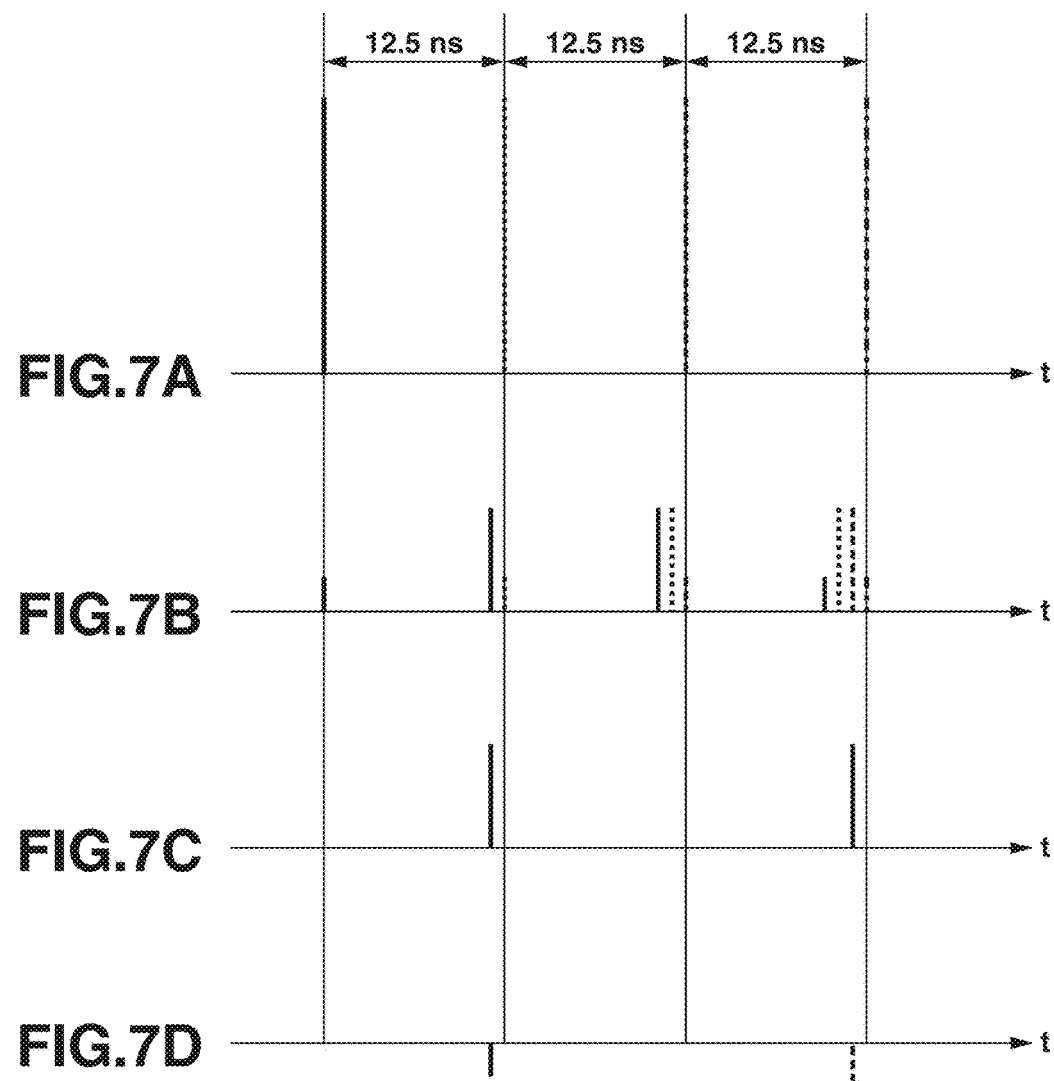
FIGS. 7A to 7D illustrate time profiles of optical pulse trains of the SRS microscope according to Example 1.

FIG. 7A illustrates an optical pulse train 31 generated by the pulse laser 501. While each pulse has a width of several picoseconds, each pulse is illustrated as a line with a length corresponding to the light intensity in FIG. 7A. The optical pulse train 31 is incident on the noise reduction apparatus 200 to generate an optical pulse train 33 having a time profile as illustrated in FIG. 7B. The delay time in the noise reduction apparatus 200 is slightly shifted from 12.5 nanoseconds to prevent interference associated with a temporal overlap with an adjacent pulse light beam. The amount of shift from 12.5 nanoseconds can be any amount equal to or greater than the pulse width, and the delay time can be changed by ten to several tens of picoseconds (exaggerated in FIG. 7B). This level of change has only an insignificant effect on the noise reduction rate.

FIG. 7C illustrates an optical pulse train 32 generated by the pulse laser 502. The wavelength ($\lambda 1$) of the optical pulse train 33 is smaller than the wavelength ($\lambda 2$) of the optical pulse train 32. If pulses of the optical pulse trains 33 and 32 coincide in timing as illustrated in FIGS. 7B and 7C and are condensed onto the same point on a sample, the intensity of a pulse light beam transmitted through the sample is changed due to SRS. The light intensity of the optical pulse train 33 having a smaller wavelength decreases when SRS occurs. FIG. 7D illustrates that the light intensity of the optical pulse train 33 has changed owing to SRS. Since the light intensity is decreased owing to SRS, the value is a minus figure. The amount of change is illustrated in an exaggerated manner, and the actual amount is a very small amount that is about $10^{-4}$ times the original pulse light intensity, so that lock-in detection is conducted.

The amount of change in lock-in detected light intensity corresponds to the SRS signal and reflects information about molecules contained in the point onto which the optical beams are condensed. For example, the SRS signal becomes large when the resonant frequency of molecular oscillation contained in the point coincides with a difference in light frequency between two lasers ($c/\lambda 1 - c/\lambda 2$), where c is the speed of light. A wavelength selection filter 503 changes $\lambda 2$, so that the SRS signal is acquired while ($c/\lambda 1 - c/\lambda 2$) is changed. In other words, a Raman spectrum is acquired. From the Raman spectrum, molecules contained in the sample can be estimated. The SRS microscope is capable of acquiring spectra equivalent to those acquired by a spontaneous Raman microscope. The scattering efficiency of SRS is much more significant than the scattering efficiency of spontaneous Raman scattering, so that the SRS microscope can acquire a Raman spectrum in a shorter time than the time needed by a spontaneous Raman scattering microscope.

In one embodiment, the wavelength selection filter 503 selects and cuts out a wavelength region with a width of about 0.3 nanometers from a wavelength range (about 40 nanometers around 1030 nanometers) of the light beam generated by the pulse laser 502, using a spectroscopic device such as a diffraction grating. The duration of a pulse light beam output by the wavelength selection filter 503 is changed to a duration corresponding to a width of 0.3 nanometers, but the time profile (repeat frequency) is maintained even after the pulse light beam passes through the wavelength selection filter 503.

The traveling direction of the optical pulse train 33 having passed through the wavelength selection filter 503 is changed at a mirror 504, and then the optical pulse train 33 is coaxially combined with the optical pulse train 32 at a dichroic mirror 505. The optical pulse train 32 is output as a parallel light beam from a collimator lens 506 to combine with the optical pulse train 32.

The SRS microscope is configured as a laser scanning microscope. The optical pulse trains 32 and 33 are coaxial and enter a beam scanner 507 to be polarized and output by the beam scanner 507. The beam scanner 507 includes a Galvano scanner and a resonant scanner and changes a direction of an optical axis into two directions which are orthogonal to each other. To simplify the illustration, two mirrors in the beam scanner 507 are illustrated as one mirror in FIG. 6. By using the resonant scanner (scan frequency 8 kHz) and the Galvano scanner (scan frequency 15 Hz), an image with 500 lines can be acquired at 30 frames per second.

The optical beam polarized by the beam scanner 507 enters an objective lens 508 through a relay lens (not illustrated). The objective lens 508 condenses the optical pulse trains 32 and 33 onto the same point on a sample 509. From the point of view of spatial resolution for SRS signal detection and the signal-to-noise ratio, the objective lens 508 may be an objective lens with a large numerical aperture (NA).

The sample 509 is sandwiched between cover glasses (not illustrated) having a thickness of several tens of micrometers to two hundred micrometers. The beam scanner 507 polarizes the optical beams to condense a light spot on the sample 509, and the light spot is two-dimensionally scanned to change the SRS signal into a two-dimensional image. The SRS signal is generated only at the condensed optical spot, so that a three-dimensional image can also be acquired by moving the sample 105 in the optical axis direction on a stage (not illustrated).

A condenser lens 510 is an objective lens or condenser lens having a NA equal to or larger than the NA of the objective lens 508 to receive all light which passes through the sample 509 and has an intensity modulated by SRS. The optical beam output from the condenser lens 510 passes through a filter 511 and a relay lens (not illustrated) and thereafter applied to a light receiving surface of a photodiode (detection device) 512. The filter 511 includes a dielectric multilayer film. The filter 511 blocks a light beam of wavelength $\lambda 2$ and transmits a light beam of wavelength $\lambda 1$. The photodiode 512 is irradiated with the optical pulse train 32 having an intensity modulated by SRS. The photodiode 512 uses a silicon photodiode which is sensitive to a light beam of 800 nanometers and has a cutoff frequency of 40 MHz or higher.

While the repeat frequency of the optical pulse train 32 is 80 MHz (pulse period: 12.5 nanoseconds), the intensity modulation by SRS is 40 MHz (period: 25 nanoseconds). A current voltage conversion circuit 513 is a filter circuit and amplification circuit configured to attenuate a large 80-MHz component contained in a current signal generated at the photodiode 512 while amplifying a weak 40-MHz component to output a voltage.

A synchronous detection circuit (e.g., lock-in amplifier) 514 is an electric circuit using a mixer. The synchronous detection circuit 514 extracts a component which is contained in the voltage signal output by the current voltage conversion circuit 513 and synchronized with the repeat frequency 40 MHz of the pulse laser 502, to output a voltage. The output voltage of the synchronous detection circuit 514 indicates the extent of SRS occurring at the condensed point on the sample 509.

A calculator 515 converts an output signal (SRS signal) from the synchronous detection circuit 514 into a two-dimensional image and displays the two-dimensional image using a control signal from the beam scanner 507. The calculator 515 can display as a three-dimensional image the SRS signal acquired by moving the sample 509 in the optical axis direction on the stage (not illustrated). Further, the calculator 515 can display a Raman spectrum from the SRS signal acquired by changing the wavelength of at least one of the two pulse lasers.

Noise near 40 MHz contained in the optical pulse train 32 is reduced over a wide frequency band by the noise reduction apparatus 200, so that high sensitivity is maintained even when 10 mega samples or more of signals are acquired per second. That is, performance limited by shot noise which is generated in principle can be provided. Further, since the light amount loss is reduced, the noise reduction apparatus 200 can irradiate the sample 509 with light with higher intensity than those according to the conventional techniques. This improves the SRS signals, which increases the sensitivity of the detection apparatus.

Figure 8:
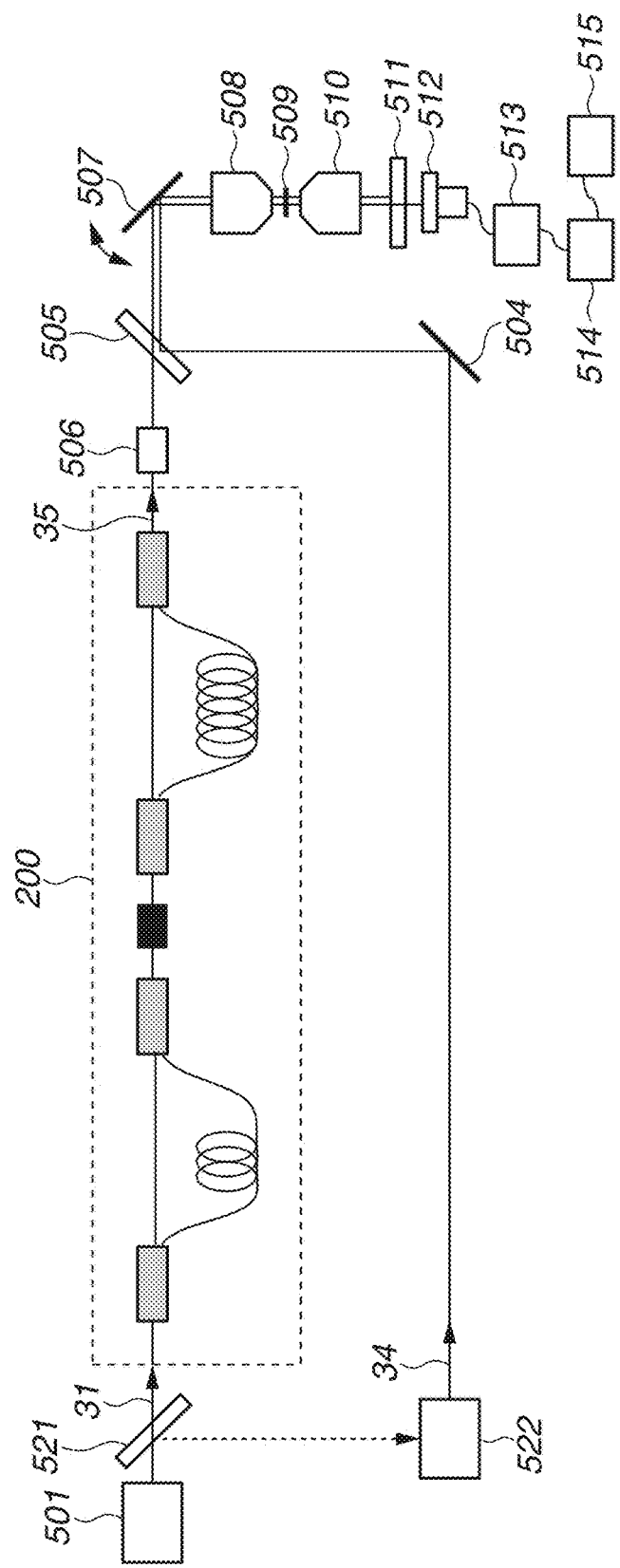
FIG. 8 is a conceptual diagram illustrating a SRS microscope according to Example 2.

A detection apparatus to which Example 2 of the disclosure is applied will be described below with reference to FIG. 8. As in Example 1, a SRS microscope will be described as an example. Description of a point that overlaps with Example 1 is omitted.

According to Example 1, the pulse periods of pulse light beams generated by the two pulse lasers are synchronized by a pulse synchronization device (not illustrated) at the ratio 1:2. According to the present example, the SRS microscope includes a single pulse laser. In other words, an example of the structure that does not use the pulse synchronization device will be described below.

An optical pulse train generated by the pulse laser 501 is divided into two optical pulse trains by a half mirror 521. One of the divided optical pulse trains is input as the optical pulse train 31 to the noise reduction apparatus 200 as in Example 1. The wavelength of the other divided optical pulse train is changed by a wavelength conversion unit 522 (second generation unit). For example, an optical parametric oscillator (OPO) can be used as a wavelength changing unit. A Raman spectrum is obtainable by changing the wavelength with use of the OPO as in Example 1.

FIG. 9A illustrates the time profile of the optical pulse train 31. FIG. 9C illustrates an optical pulse train 34 having the wavelength changed by the OPO. The optical pulse trains 31 and 34 both have a repeat frequency of 80 MHz, so that SRS occurs at 80 MHz. As in Example 1, when SRS signal detection by lock-in is attempted, the intensity of the optical pulse train itself is evaluated, so that SRS detection with great sensitivity is not successfully conducted.

To address this situation, the noise reduction apparatus according to the present example reduces the 80 MHz component of the intensity of the optical pulse train to successfully conduct SRS signal detection by lock-in.

To reduce noise at 80 MHz, the time interval of pulse light beams divided by the noise reduction apparatus 200 is set to 6.25 nanoseconds. To produce the time interval, a difference in fiber length in the first delaying/combining unit of the noise reduction apparatus 200 is set to 1.25 meters (the speed of light is $3\times10^8$ meters per second, and the group refractive index of optical fibers is 1.5). Further, a difference in fiber length in the second delaying/combining unit is set to 2.5 meters.

This operation corresponds to the doubling of the repeat frequency of 80 MHz of the optical pulse train (the doubling to 160 MHz), however, a variation of intensity is reduced compared to the case of simply dividing the optical pulse train into two trains to double the frequency. This effect is similar to the noise reduction rate illustrated in FIG. 4, and the variation of intensity is more reduced in the case of four branches than in the case of two branches.

The time interval of the pulse light beam divided by the noise reduction apparatus 200 may be set to (6.25+12.5·m) nanoseconds (m is an integer of 0 or greater). However, the larger the value of m is, the narrower the frequency range over which noise can be reduced becomes, and the larger lengths of the optical fibers of the noise reduction apparatus are to be, so that there is no merit.

FIG. 9B illustrates an optical pulse train 35 generated by the noise reduction apparatus 200. FIG. 9D illustrates the light intensity of the optical pulse train 35 which is changed by SRS. A change in light intensity caused by SRS is detectable with the lock-in amplifier having as a lock-in frequency the repeat frequency of 80 MHz of the pulse light beam generated by the pulse laser 501. A method for the detection is similar to the method according to Example 1 except for the lock-in frequency.

Figure 10:
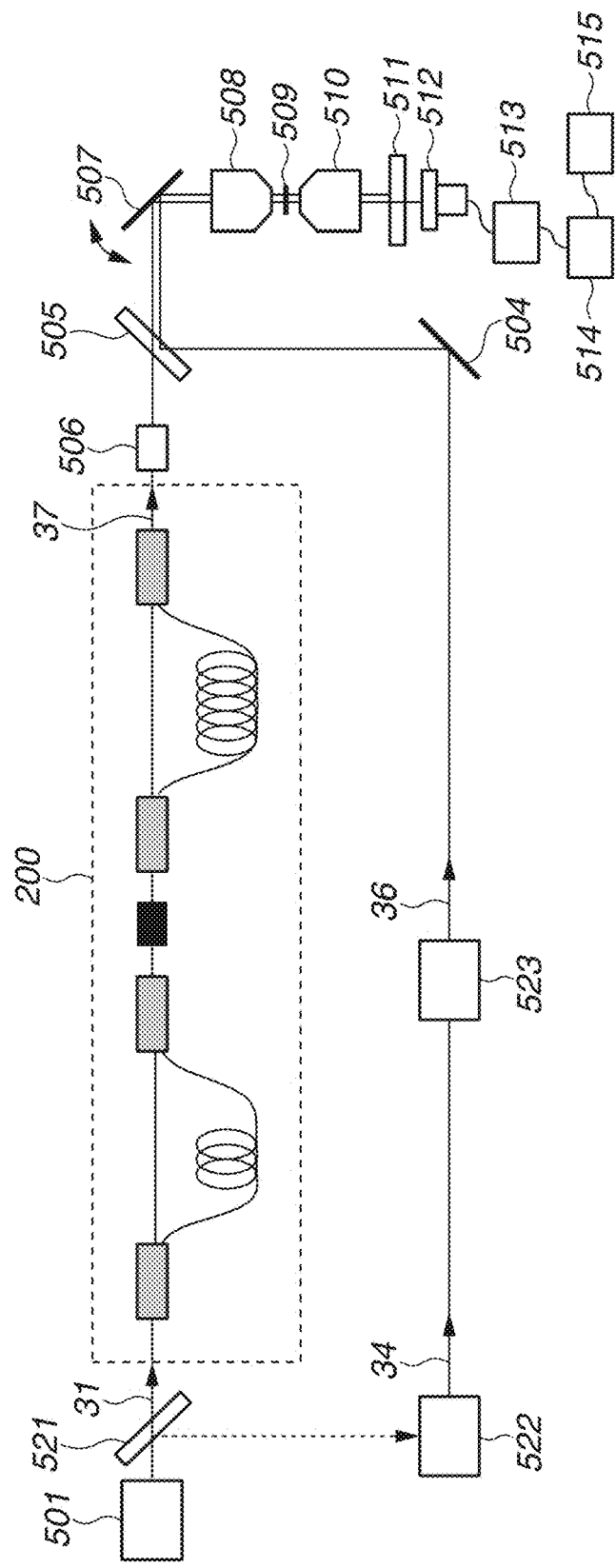
FIG. 10 is a conceptual diagram illustrating a SRS microscope according to Example 3.

A detection apparatus to which Example 3 of the disclosure is applied will be described below with reference to FIG. 10. As in Examples 1 and 2, a SRS microscope will be described as an example. Description of a point that overlaps with Example 1 is omitted.

According to Example 1, SRS signal detection by lock-in is conducted using as a lock-in frequency the repeat frequency generated by the pulse laser 502. According to Example 1, SRS signal detection by lock-in is conducted using as a lock-in frequency the repeat frequency generated by the pulse laser 501.

In the present example, an example in which a pulse light beam is modulated at a desired frequency using an external modulation device to modulate an occurrence of SRS and conduct SRS signal detection by lock-in will be described.

As in Example 2, a single pulse laser is included, and one of the two pulse light beams divided by a half mirror 521 is passed through the wavelength conversion unit 522 (third generation unit) to change the wavelength. A modulation unit 523 modulates either an optical path length, light intensity, or polarization direction of the pulse light beam contained in the optical pulse train 34 output from the wavelength conversion unit 522. If the timings of two pulse light beams at the sample do not correspond, the SRS signal decreases. Thus, if the optical path length of the pulse light beam is modulated, the SRS signal varies in synchronization. SRS occurs proportional to the product of intensities of two pulse light beams, so that if the light intensity of one of the pulse light beams is modulated, the SRS signal varies in synchronization. The SRS signal reaches a maximum intensity when the polarized light beams of the two pulse light beams correspond. Thus, if the polarization direction is modulated, the SRS signal varies in synchronization.

Specifically, SRS signal detection can be conducted by lock-in using as a lock-in frequency a frequency for modulating the pulse light beams. While the modulation frequency can be any frequency, the higher the frequency, the less an effect of light source noise such as 1/f noise, and the wider a signal band acquirable by the lock-in amplifier. The modulation unit 523 can include an electric optical device such as a Pockels cell. The noise reduction apparatus according to the present example is applicable when conducting SRS signal acquisition by the lock-in detection with high sensitivity.

As an example, the modulation unit 523 modulates the light intensity at a frequency which is one fourth of the repeat frequency of the pulse light beam generated by the pulse laser 501. FIG. 11C illustrates the time profile of the pulse light beam output from the modulation unit 523.

As illustrated in FIG. 11D, the SRS signal is modulated and generated at 20 MHz. Thus, the noise reduction apparatus according to the present example reduces noise near 20 MHz which is contained in the detect target pulse light beam, so that signal detection with high sensitivity is realized.

To reduce noise near 20 MHz, the time interval of the pulse light beam divided by the noise reduction apparatus 200 is set to 25 nanoseconds. To produce the time interval, a difference in fiber length in the first delaying/combining unit of the noise reduction apparatus 200 is set to 5 meters (the speed of light is $3 \times 10^8$ meters per second, and the group refractive index of optical fibers is 1.5). Further, a difference in fiber length in the second delaying/combining unit is set to 10 meters.

FIG. 11A illustrates the time profile of the optical pulse train 31 input to the noise reduction apparatus 200. FIG. 11B illustrates the time profile of an optical pulse train 37 output from the noise reduction apparatus 200. A change in light intensity caused by SRS is detectable with the lock-in amplifier having as a lock-in frequency the modulation frequency of 20 MHz of the pulse light beam by the modulation unit 523. A method for the detection is similar to the method according to Example 1 except for the lock-in frequency.

In a case of modulating a pulse light beam with a period which is N (N is an integer of one or greater) times the pulse period of the pulse light beam generated by the pulse laser, noise near the lock-in frequency is reduced if the time interval of the divided pulse generated by the noise reduction apparatus is set to N/2 of the pulse period. That is, the two delay times are each set to N/2 times the pulse period and N times the pulse period.

For example, an exemplary embodiment of the disclosure is applicable to an optical microscope to detecting light generated by a non-linear optical phenomenon such as coherent anti-Stokes Raman scattering (CARS) or multiphoton excitation (especially, two-photon excitation) fluorescence. Further, an exemplary embodiment of the disclosure is applicable to detection of light modulated by a non-linear optical phenomenon such as multiphoton absorption (especially, two-photon absorption). Further, according to the above-described exemplary embodiments, the polarization direction is rotated by 60 degrees by the polarization adjustment unit (5, 15). However, the polarization adjustment unit can be omitted by relatively rotating the two delaying/combining optical paths about the optical axis.

The phrases "the intensity ratio of the first pulse light beam to the second pulse light beam is 1:1", "the intensity ratio of the third pulse light beam to the fourth pulse light beam is 1:3", and "the intensity ratio of the fifth pulse light beam to the sixth pulse light beam is 3:1" each encompass cases in which the specified intensity ratio is not satisfied. More specifically, even in a case in which at least one of the third to sixth pulse light beams is increased or decreased by 10% with respect to the light intensity before the dividing, a benefit of the disclosure is still produced, so the above-described phrases encompass such a case.

Further, the phrase "the delay time ratio of the first delay time to the second delay time is 1:2 or 2:1" encompasses a case in which the time ratio is not satisfied. More specifically, a benefit of the disclosure is produced if $|\tau_1-\tau_2/2|<\tau_1/6$ is satisfied when the ratio of the first delay time $\tau_1$ to the second delay time $\tau_2$ is 1:2. Further, a benefit of the disclosure is produced if $|\tau_1/2-\tau_2|<\tau_2/6$ is satisfied when the ratio of the first delay time $\tau_1$ to the second delay time $\tau_2$ is 2:1. Thus, the above-described phrases encompass the cases.

While the disclosure has been described with reference to exemplary embodiments, it is to be understood that the disclosure is not limited to the disclosed exemplary embodiments. The scope of the following claims is to be accorded the broadest interpretation so as to encompass all such modifications and equivalent structures and functions.

What is claimed is:

1. A noise reduction apparatus comprising:
a first delaying/combining unit configured to branch a pulse light beam of a first period into two pulse light beams, provide a first delay time between the two branched pulse light beams, and combine the two branched pulse light beams, to output a first pulse light beam polarized in a first direction and a second pulse light beam polarized in a direction orthogonal to the first direction and delayed by the first delay time with respect to the first pulse light beam;
a second delaying/combining unit configured to branch the first pulse light beam into two pulse light beams, provide a second delay time between the two branched pulse light beams, combine the two branched pulse light beams, to output a third pulse light beam polarized in a second direction and a fourth pulse light beam polarized in a direction orthogonal to the second direction and delayed by the second delay time with respect to the third pulse light beam, branch the second pulse light beam into two pulse light beams, provide the second delay time between the two branched pulse light beams, and combine the two branched pulse light beams, to output a fifth pulse light beam polarized in the second direction and a sixth pulse light beam polarized in a direction orthogonal to the second direction and delayed by the second delay time with respect to the fifth pulse light beam, and
a polarization adjustment unit configured to adjust a polarization direction of the first pulse light beam and a polarization direction of the second pulse light beam, wherein the polarization adjustment unit is located between the first delaying/combining unit and the second delaying/combining unit.

2. The noise reduction apparatus according to claim 1, wherein the polarization adjustment unit rotates the polarization direction of the first pulse light beam and the polarization direction of the second pulse light beam configured to branch the first pulse light into the third pulse light beam and the forth light beam in a certain light intensity ratio and to branch the second pulse light beam into the sixth light beam and the fifth light beam in the certain light intensity ratio at the second delaying/combining unit.

3. The noise reduction apparatus according to claim 2, wherein the certain light intensity ratio is approximately 1:3.

4. The noise reduction apparatus according to claim 2, wherein the polarization adjustment unit rotates the polarization direction of the first pulse light beam and the polarization direction of the second pulse light beam in a common rotation angle.

5. The noise reduction apparatus according to claim 4, wherein the common rotation angle is approximately 30 degrees or 60 degrees.

6. The noise reduction apparatus according to claim 1, wherein the polarization adjustment unit includes a half-wave plate or a fused portion fused between a pair of optical fiber ends.

7. The noise reduction apparatus according to claim 1, wherein the first delaying/combining unit includes a branching polarization beam splitter and a combining polarization beam splitter, and
the combining polarization beam splitter combines the first pulse light beam and the second pulse light beam, each of which is a linearly-polarized light beam.

8. The noise reduction apparatus according to claim 1, wherein a light intensity ratio between the first pulse light beam and the second pulse light beam is approximately 1:1.

9. The noise reduction apparatus according to claim 1, wherein the second delaying/combining unit includes a branching polarization beam splitter and a combining polarization beam splitter, and
the combining polarization beam splitter combines the third pulse light beam, the forth pulse light beam, the fifth pulse light beam and the sixth pulse light beam, each of which is a linearly-polarized light beam.

10. The noise reduction apparatus according to claim 1, wherein the first delaying/combining unit provides the first delay time according to a difference in length of a polarization maintaining fiber.

11. The noise reduction apparatus according to claim 1, wherein the second delaying/combining unit provides the second delay time according to a difference in length of a polarization maintaining fiber.

12. The noise reduction apparatus according to claim 1, further comprising a polarization maintaining fiber between the first delaying/combining unit and the second delaying/combining unit,
wherein the polarization maintaining fiber includes a fused portion which is configured to change a polarization direction of a pulse light beam, and
wherein the polarization adjustment unit is the fused portion.

13. The noise reduction apparatus according to claim 1, wherein a shorter one of the first delay time and the second delay time is N/2 times the first period and a longer one of the first delay time and the second delay time is N times the first period, where N is an integer of 1 or greater.

14. The noise reduction apparatus according to claim 1, wherein the first period is associated with a repetition period which is an inverse number of a repetition frequency of the pulse light beam from a light source.

15. The noise reduction apparatus according to claim 1, wherein a delay time ratio between the first delay time and the second delay time is 1:2 or 2:1.

16. A detection apparatus comprising:
the noise reduction apparatus according g to claim 1;
a first generation unit configured to generate the pulse light beam with the first period;
an irradiation unit configured to irradiate a sample with the pulse light beam via the noise reduction apparatus; and
a detection device configured to detect a light beam from the sample.

17. The detection apparatus according to claim 16, further comprising a second generation unit configured to generate a pulse light beam with a second period,
wherein the irradiation unit irradiates the sample with the pulse light beam generated by the first generation unit via the noise reduction apparatus and the pulse light beam generated by the second generation unit, and
wherein the detection device detects a light beam modulated with the second period.

18. The detection apparatus according to claim 17, wherein the second period is N times the first period, where N is an integer of 1 or greater.

19. The detection apparatus according to claim 17, further comprising a lock-in amplifier configured to determine as a lock-in frequency a frequency corresponding to the second period.

20. The detection apparatus according to claim 16, further comprising:
a third generation unit configured to generate a pulse light beam with the first period; and
a modulation unit configured to modulate at least one of an optical path length, light intensity, and polarization direction of the pulse light beam generated by the third generation unit, with a period which is N times the first period,
wherein the irradiation unit irradiates the sample with the pulse light beam generated by the first generation unit via the noise reduction apparatus and the pulse light beam generated by the third generation unit via the modulation unit, and the detection device detects a light beam modulated with the period which is N times the first period.

21. The detection apparatus according to claim 20, further comprising a lock-in amplifier configured to determine as a lock-in frequency a frequency corresponding to the period which is N times the first period.

22. The detection apparatus according to claim 16, wherein the modulated light beam is a light beam generated by two-photon excitation at the sample, a light beam generated by multiphoton excitation at the sample, a light beam generated by non-linear Raman scattering at the sample, a pulse light beam generated by the first generation unit with intensity modulated by two-photon absorption at the sample, a pulse light beam generated by the first generation unit with intensity modulated by multiphoton absorption at the sample, or a pulse light beam generated by the first generation unit with intensity modulated by stimulated Raman scattering at the sample.

23. The detection apparatus according to claim 16, wherein the noise reduction apparatus further comprises a polarization adjustment unit configured to adjust the polarization direction of the first pulse light beam and the polarization direction of the second pulse light beam.

24. The detection apparatus according to claim 16, wherein the first delaying/combining unit second delaying/combining unit each includes a polarization beam splitter.

25. The detection apparatus according to claim 16, wherein the first delaying/combining unit provides the first delay time according to a difference in length of a polarization maintaining fiber and the second delaying/combining unit provides the second delay time according to a difference in length of a polarization maintaining fiber.

26. The detection apparatus according to claim 16, wherein one of the first delay time and the second delay time that is shorter than another delay time, is N/2 times the first period, where N is an integer of 1 or greater.

* * * * *